United States Patent [19]

Rackley

[11] Patent Number: 4,867,679

[45] Date of Patent: Sep. 19, 1989

[54] ORTHODONTIC LIGATURE

[75] Inventor: Robert L. Rackley, Parkersburg, W. Va.

[73] Assignee: E. I. Du Pont de Nemours and Company, Wilmington, Del.

[21] Appl. No.: 182,729

[22] Filed: Apr. 18, 1988

[51] Int. Cl.$^4$ .............................................. A61C 3/00
[52] U.S. Cl. ........................................ 433/15; 433/11; 132/321
[58] Field of Search ............................. 433/15, 11, 18; 132/321

[56] References Cited

U.S. PATENT DOCUMENTS

| | | | |
|---|---|---|---|
| 3,091,856 | 6/1963 | Goldstein | 433/18 |
| 4,373,914 | 2/1983 | Colbert | 433/18 |
| 4,522,590 | 6/1985 | Pletcher | 433/15 |
| 4,584,240 | 4/1986 | Herbert et al. | 428/373 |
| 4,725,229 | 2/1988 | Miller | 433/11 |

*Primary Examiner*—John J. Wilson
*Attorney, Agent, or Firm*—Donald W. Huntley

[57] ABSTRACT

An orthodontic device comprising filament and one or more retaining sheaths through which the filament is looped, useful for retaining wires on orthodontic brackets.

8 Claims, 3 Drawing Sheets

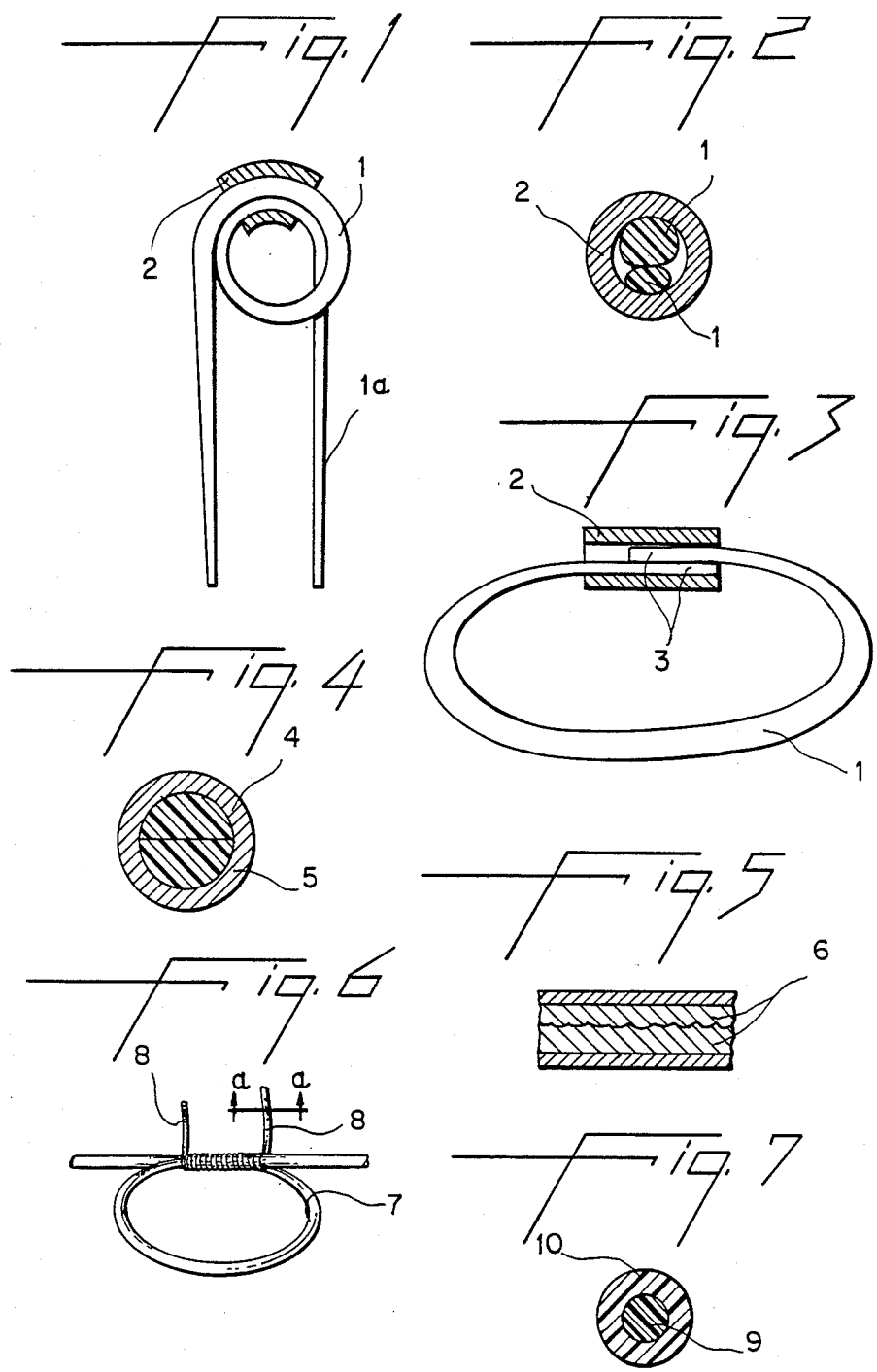

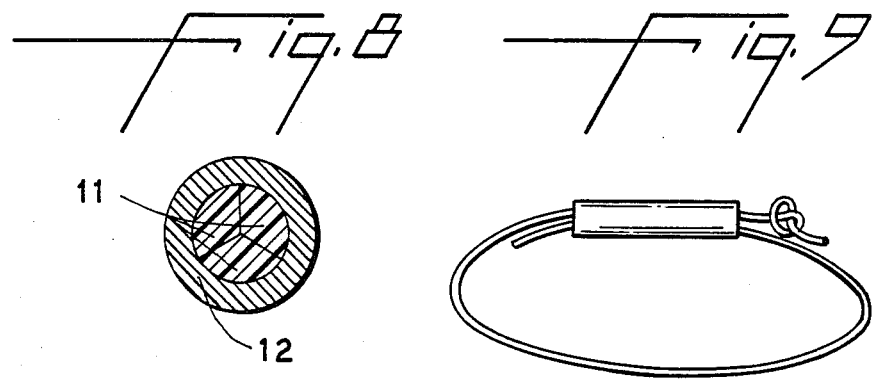
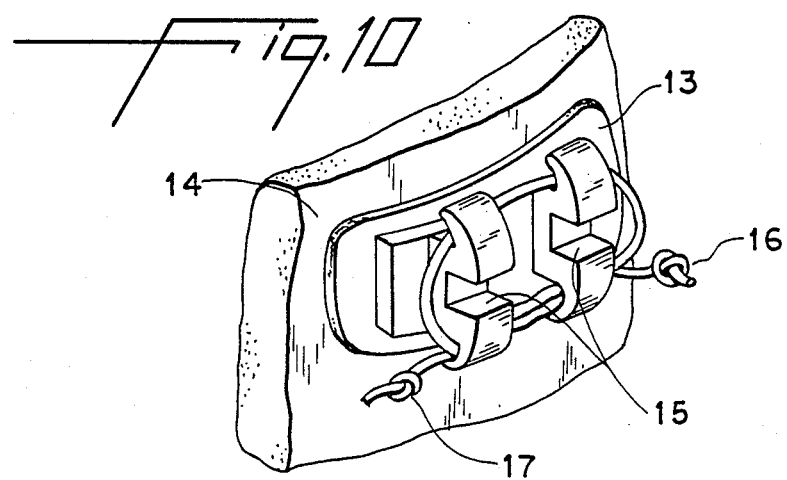
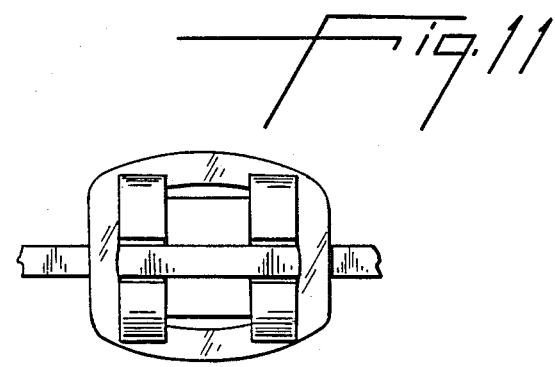

b          a

19

//<br>
ORTHODONTIC LIGATURE

BACKGROUND OF THE INVENTION

In orthodontics, various devices are used for implementing tooth movement. Brackets are bonded to each tooth and forces and couples are applied to the teeth by archwires and elastic devices such as rubber bands. An important element in these devices is the ligature, which holds the bracket in contact with the archwire.

There are three types of ligatures that are currently used. The first is wire which is twisted around the bracket and archwire and cut with snips. The sharp ends and the time consumed during installation are problems, but the retention force is very high. The second type of ligature is a small o-ring that is difficult to install even with special tools. While these o-ring ligatures are most commonly used, their retention force is low. A third type of ligature uses braided elastomeric thread and extruded tubing which is tied to the various devices with knots.

Each of the above ligatures requires a great deal of time to install. Accordingly, a continuing need exists for ligatures which are easier to apply and which provide holding power which is equivalent to or better than previously available devices. A further need exists for improved ligatures to provide tensile forces between teeth.

SUMMARY OF THE INVENTION

The present invention provides a ligature which has a high retention force and is easily installed.

Specifically, the instant invention provides an orthodontic ligature comprising a filament and a retaining sheath, the filament being looped at least once through the retaining sheath, the retaining sheath having internal dimensions closely approximating the combined outer diameters of the filament looped through the sheath.

BRIEF DESCRIPTION OF THE DRAWINGS

FIG. 1 is an illustration of a ligature of the present invention.

FIG. 2 is a cross-sectional view of a ligature of the present invention, taken through the retaining sheath.

FIG. 3 illustrates an assembly technique that can be used to prepare the ligatures of the present invention.

FIG. 4 is a cross-sectional illustration of another embodiment of the present invention which provides greater interfacial contact between the filaments.

FIG. 5 is a cross-sectional illustration of another embodiment of the present invention in which the surfaces of the filaments are serrated.

FIG. 6 is an illustration of an alternative technique for preparing the ligatures of the present invention.

FIG. 7 is a cross-sectional illustration of the coextruded filament used in the preparation technique of FIG. 6.

FIG. 8 is a cross-sectional illustration of another embodiment of the present invention.

FIG. 9 is an illustration of an embodiment of the present invention in which one end of the filament is knotted.

FIG. 10 is an illustration of an orthodontic bracket mounted on a tooth, in combination with a ligature of the present invention.

FIG. 11 is an illustration of the o-ring ligature previously used in the art.

DETAILED DESCRIPTION OF THE INVENTION

Figure 12:
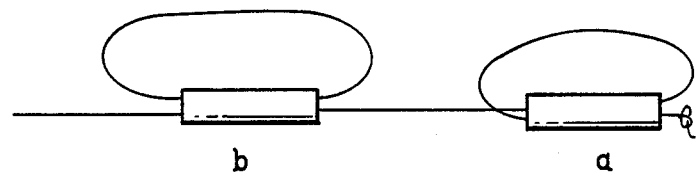
FIG. 12 is an illustration of the present ligatures in a multiple configuration for application to two separate teeth.

The ligatures of the present invention comprise a filament and a retaining sheath, the filament being looped at least once through the retaining sheath, the retaining sheath having internal dimensions closely approximating the combined outer diameters of the filaments looped through the sheath. Preferably, the internal dimensions conform closely to the outer configuration of the filaments.

The filaments are preferably prepared from thermoplastic polymers. A wide variety of polymers can be used, including, for example, polyesters, polyamides, fluoropolymers, and copolyetheresters. The polymeric filaments are preferably oriented by drawing about from 3.0 to 6 times their original longitudinal dimension, to increase their tensile strength to at least about 170 MPa.

The diameter of the filament will vary with the type of bracket used, but will generally be about from 3 to 30 mils, or about from 0.067 to 0.67 mm.

The material used for the retaining sheath can e the same or different than the filament. However, a polymeric or elastomeric material for the sheath is particularly preferred to provide the holding power to retain the filament. An important consideration in the preparation of the sheath is that its internal diameter be no greater than the combined diameters of the filaments that are looped through the sheath. The extent to which the diameter of the sheath is less than the combined diameters of the filaments will depend on the strength of the sheath material, the elastomeric nature of the sheath material and the holding force that is desired for the filaments.

Polymeric filaments having a sheath-core construction, as described, for example, in Herbert et al., U.S. Pat. No. 4,584,240, hereby incorporated by reference, are particularly preferred materials for the sheath, especially when the sheath is formed in situ as described below.

The basic construction of the present ligatures is illustrated in FIG. 1, in which monofilament 1 is looped through retaining sheath 2. FIG. 2 is a cross-sectional illustration of the ligature of FIG. 1.

The construction of the present ligatures can accomplished using a variety of techniques. One such technique is illustrated in FIG. 3, wherein a tapered monofilament 1 is used with ends 3 sufficiently small to pass through the sheath. The small ends of the monofilament are threaded through the sheath, as shown, and then drawn tight to form the required loop.

The filaments used in the present invention are generally round in cross-section. However, other configurations can be effectively used, as illustrated in FIG. 4, which is a cross-sectional illustration of another embodiment of the present invention. There, the filaments 4 have a semi-circular configuration, which occupies the space within the sheath 5 more fully and provides more surface interaction. FIG. 5 is a longitudinal cross-section of a further embodiment of the invention in which the filaments 6 have a cross-sectional configuration similar to that of FIG. 4, but wherein the opposing filament surfaces are serrated.

While the retaining sheath of the present ligatures can be preformed, it can also be made in situ, through the use of polymers for the sheath that have a melting or softening point lower than that of the filament. Construction of the sheath using this technique is illustrated in FIG. 6. There, a loop of monofilament 7 is formed, around which is wrapped of coextruded monofilament 8 having a core of polymer having a relatively high melt temperature and an outer layer of polymer having a relatively low melt temperature. The coextruded monofilament is shown in FIG. 7, which is a section taken through a—a of FIG. 6. The coextruded monofilament has core 9 and outer layer 10. After wrapping or winding the coextruded monofilaments around the loop, they are heated above the melting point of the outer layer to form the retaining sheath around the loop. By the in situ formation of the sheath, it closely conforms to the combined outer diameters of the filaments, thereby maximizing the retaining power of the ligature.

In a similar way, the sheath can be injection molded around the looped filaments, or by molding thermosetting polymers around the filaments.

FIG. 8 is a cross-sectional illustration of another embodiment of the present invention in which three sections of monofilament 11 are looped through the sheath. As will be evident to the skilled practicioner, any number of monofilaments can be used which is consistent with the ability to tighten the ligature upon installation.

FIG. 9 shows a ligature of the present invention in which one end is knotted. In this way, when applying the ligature, there is only one end that has to be pulled to tighten the ligature around the bracket. If it is desired to knot both ends of the ligature, it has been found convenient to knot one end, as shown in FIG. 9, after which the other end of the filament is pulled tight. Then a knot at the second end is formed and slipped down to the other end of the retaining sheath with a small diameter rod or other tool.

FIG. 10 is an illustration of a ligature of the present invention applied on a bracket 13 which is mounted on tooth 14. The archwire, normally positioned in notches 15, is eliminated for clarity. The ligature is secured with a first knot at end 16 and a second knot at end 17, which is a preferred method of attachment. After knotting, the remaining part of the filament is cut off and discarded.

FIG. 11 is an illustration of an orthodontic bracket with the common o-ring ligature of the type previously used in the art. It is this ligature which is used in Comparative Example A below.

Figure 13:
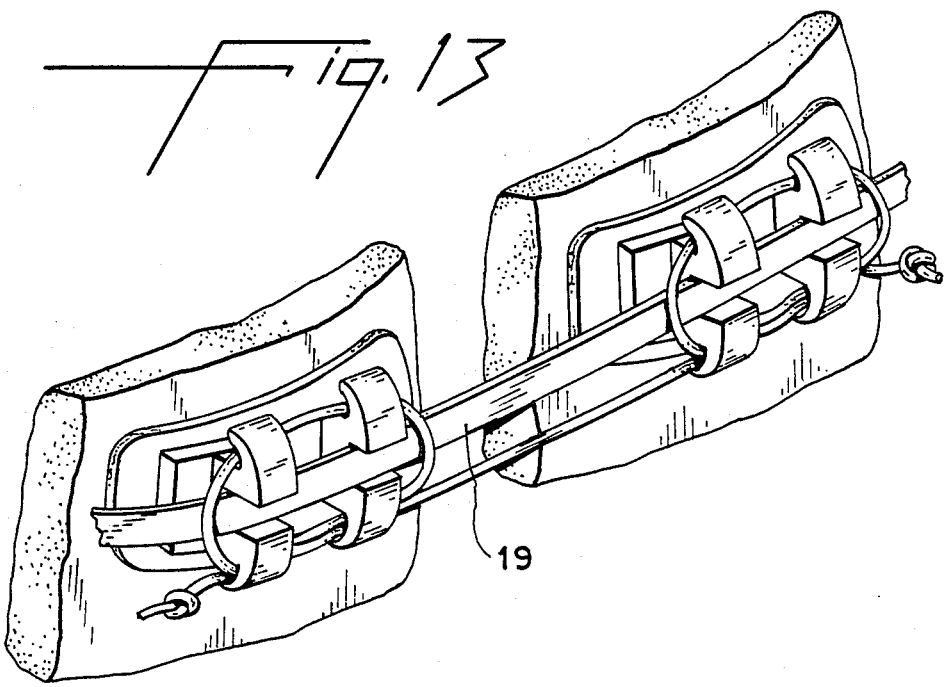
FIG. 13 is an illustration of two teeth engaged with the ligatures of the present invention.

The ligatures of the present invention can be used in ganged form, as shown in FIG. 12, and used to anchor the archwires on two separate teeth. Such an arrangement is more fully illustrated in FIG. 13, in which archwire 19 is attached to the brackets on two teeth with a ligature as shown in FIG. 14. The ligature can be applied to one tooth, such as a rear molar, and wrapped around additional brackets on adjacent teeth, until the opposite molar is reached to connect all brackets on a top or bottom archwire with a single ligature. Using an elastic monofilament can apply forces between two teeth as well as holding a bracket and arch wire together.

The ligatures of the present invention provide holding power that is comparable to the o-rings typically used in ligatures, while providing markedly greater ease of installation. The holding power is greatly enhanced by a knot, and can be improved by cutting the free end with a hot knife. The holding power of the ligatures can be further enhanced with the application of adhesive. For example, an adhesive can be applied after installation instead of having a knot tied. Alternatively, an adhesive can be applied to the ligatures before installation, with cold storage of the ligature to prevent curing, and permitting the heat of the mouth to cure the adhesive after installation. The ligatures of the present invention, in addition to their benefits to orthodontics, can be useful in other applications such as surgery, as will be evident to those skilled in the art.

EXAMPLES 1-19 AND COMPARATIVE EXAMPLE A

In the following Examples and Comparative Example, a procedure was developed to test ligatures. The circumference around the inside surface of a typical dental bracket is about 13 mm, and the outside circumference of the bracket wings is about 18 mm. Accordingly, the force required to stretch a ligature from 13 to 18 mm is defined as the "holding power". A round mounting fixture was made for ligatures to be tested. The fixture had a diameter of 13 mm., and had grooves which permitted the insertion of hooks to grip the ligature on opposite sides of the fixture. The fixture was placed in an Instron testing apparatus and the force to move the Instron jaws 2.5 mm inch apart was noted. This simulates the force to stretch a ligature enough to come off the tie wings of a dental bracket.

In the Examples, ligatures were assembled using tapered and level monofilament, as indicated in the Table. The monofilaments were prepared from the materials, an exhibited the diameters indicated in the Table. The ligatures of Examples 1-6 were prepared by threading small end of the tapered monofilament into a retaining tube or sheath having the composition and dimensions indicated in the Table. The ligatures of Examples 7-19 were prepared by first forming a loop of the monofilament, and then wrapping coextruded monofilament around the loop several times and heating for a time sufficient to fuse the coextruded monofilament into a continuous sheath around the looped, single-component monofilament. Examples 8, 10 and 19 were knotted. Examples 14 and 16 were hot knife cut. In Example 12, serrations were formed on the flat side of the monofilament having a D-shaped cross-section.

In Comparative Example A, an o-ring of the type typically used in orthodontic applications was tested.

The various ligatures were tested as described above and the force to stretch each ligature is reported in the Table.

On the basis of these results, it can be seen that the use of the coextruded monofilaments to form the outside tube increases the holding power because the closer fit between the monofilament and tube. Similarly, the serration of the filaments used in Example 12 increase the holding power. The knotted ligatures of Examples 8 and 10 and the hot knife cut Examples 14 and 16 improved holding power.

| Example | Sheath Type | OD (mm) | ID (mm) | Material | Length (mm) | Filament Element | Diam. (mm) | Material | Force to Stretch (N) |
|---|---|---|---|---|---|---|---|---|---|
| 1 | Tube | .76 | .26 | Polyurethane | 3.8 | Tapered Mono | .31 | PET | 3.9 |
| 2 | Tube | .76 | .26 | Polyurethane | 3.6 | Tapered Mono | .29 | PET | 2.2 |
| 3 | Tube | .76 | .26 | Polyurethane | 2.5 | Tapered Mono | .28 | Copolyether-ester | 2.6 |
| 4 | Tube | 1.0 | .59 | Polyethylene | 5.1 | Tapered Mono | .50 | 612 Nylon | 2.6 |
| 5 | Tube | 1.0 | .59 | Polyethylene | 6.4 | Tapered Mono | .50 | 612 Nylon | 6.6 |
| 6 | Tube | .76 | .26 | Polyurethane | 2.6 | Tapered Mono | .50 | 612 Nylon | 13.2 |
| 7 | Coextruded Mono | 1.0 | N/A | Copolyether-ester | 2.5 | Mono | .31 | Copolyether-ester | 3.3 |
| 8 | Coextruded Mono | 1.0 | N/A | Copolyether-ester | 2.5 | Mono | .31 | Copolyether-ester | 9.9 |
| 9 | Coextruded Mono | 1.0 | N/A | Copolyether-ester | 2.5 | Mono | .31 | PET | 3.3 |
| 10 | Coextruded Mono | 1.0 | N/A | Copolyether-ester | 2.5 | Mono | .31 | PET | >20 |
| 11 | Coextruded Mono | 1.2 | N/A | Copolyether-ester | 2.5 | Mono | .38 × .82 mm D-Shaped | 66 Nylon | 3.3 |
| 12 | Coextruded Mono | 1.2 | N/A | Copolyether-ester | 2.5 | Mono | .38 × .82 mm D-Shaped | 66 Nylon | 6.6 |
| 13 | Coextruded Mono | .8 | N/A | Copolyether-ester | 1.34 | Mono | .22 | Copolyether-ester | 9.0 |
| 14 | Coextruded Mono | 0.8 | N/A | Copolyether-ester | 1.34 | Mono | .22 | Copolyether-ester | >20 |
| 15 | Coextruded Mono | 0.8 | N/A | Copolyether-ester | 1.34 | Mono | .22 | Nylon 612 | 7.5 |
| 16 | Coextruded Mono | 0.8 | N/A | Copolyether-ester | 1.34 | Mono | .22 | Nylon 612 | >20 |
| 17 | Coextruded Mono | 0.8 | N/A | Nylon 12/ Nylon 612 | 1.3 | Mono | .22 | Copolyether-ester | 2.25 |
| 18 | Coextruded Mono | 0.8 | N/A | Copolyether-ester | 1.3 | Mono | .35 | Teflon ® PFA | 2 |
| 19 | Coextruded Mono | 0.8 | N/A | Copolyether-ester | 1.3 | Mono | .35 | Teflon ® PFA | >10 |
| A | O-Ring | | | "Power O" | | | | | 4.4 |

I claim:

1. An orthodontic device comprising a filament and a retaining sheath, the filament being looped at least once through the retaining sheath, the sheath covering a portion of the resulting filament loop, and at least two separate sections of the filament being within the sheath, the retaining sheath having internal dimensions closely approximating the combined outer diameters of the separate sections of filament looped through the sheath.

2. An orthodontic device of claim 1 wherein the filament is a monofilament.

3. An orthodontic device of claim 2 wherein the monofilament is thermoplastic.

4. An orthodontic device of claim 1 wherein the monofilament is prepared from elastomeric material.

5. An orthodontic device comprising at least two retaining sheaths, and a continuous filament looped at least once through each retaining sheath, each sheath covering a portion of the corresponding resulting filament loop, and at least two separate sections of the filament being within each sheath, each retaining sheath having internal dimensions which closely approximate the combined outer diameters of the separate sections of filament looped through the sheath.

6. An orthodontic device of claim 5 wherein the filament is a monofilament.

7. An orthodontic device of claim 5 wherein the filament is an elastomeric material.

8. An orthodontic device of claim 5 wherein the filament is prepared from thermoplastic.

* * * * *